United States Patent [19]
Hofmann

[11] Patent Number: 5,439,440
[45] Date of Patent: Aug. 8, 1995

[54] ELECTROPORATION SYSTEM WITH VOLTAGE CONTROL FEEDBACK FOR CLINICAL APPLICATIONS

[75] Inventor: Gunter A. Hofmann, San Diego, Calif.

[73] Assignee: Genetronics, Inc., San Diego, Calif.

[21] Appl. No.: 42,039

[22] Filed: Apr. 1, 1993

[51] Int. Cl.⁶ ............................................. A61N 1/30
[52] U.S. Cl. ......................................... 604/20; 604/49
[58] Field of Search ........................... 604/20, 21, 49; 128/898; 607/115, 116; 435/173, 287; 606/48, 50, 51

[56] References Cited

U.S. PATENT DOCUMENTS

| | | | |
|---|---|---|---|
| 4,528,265 | 7/1985 | Becker | 604/20 |
| 4,784,737 | 11/1988 | Ray et al. | 604/21 |
| 4,955,378 | 9/1990 | Grasso | 604/20 |
| 5,019,034 | 5/1991 | Weaver et al. | 604/20 |
| 5,128,257 | 7/1992 | Baer | 435/173 |
| 5,273,525 | 12/1993 | Hofmann | 604/21 |

FOREIGN PATENT DOCUMENTS 8910690  11/1989  WIPO .................... 604/20

Primary Examiner—C. Fred Rosenbaum
Assistant Examiner—Mark Bockelman
Attorney, Agent, or Firm—Baker, Maxham, Jester & Meador

[57] ABSTRACT

A method and apparatus are provided for introducing macromolecules such as genes and pharmacological compounds into cells of a patient for therapeutic purposes. An apparatus for the therapeutic application of electroporation to a portion of the anatomy of a patient, includes adjustably spaced electrodes for generating an electric field at a preselected location within a body of a patient, a sensor for generating a distance signal proportionate to the space between the electrodes, and an electrical signal generator responsive to the distance signal for applying an electric signal to the electrodes for causing the repeated generation of electric fields of a predetermined amplitude and duration forcing the walls of preselected cells in the body portion to be transiently permeable for permitting the macromolecules to enter the preselected cells.

16 Claims, 4 Drawing Sheets

ELECTROPORATION SYSTEM WITH VOLTAGE CONTROL FEEDBACK FOR CLINICAL APPLICATIONS

BACKGROUND OF THE INVENTION

The present invention relates to the treatment of ailments in humans and other mammals, and more particularly, to a method and apparatus for delivering pharmaceutical compounds and genes into live cells of a patient.

It has long been known that it would be desirable to target certain cells within the body with specific pharmaceutical compounds. For example, in the treatment of certain types of cancer with chemotherapy it is necessary to use a high enough dose of a drug to kill the cancer cells without killing an unacceptably high number of normal cells. If the chemotherapy drug could be inserted directly inside the cancer cells, this objective could be achieved. However, some of the best anti-cancer drugs, for example, bleomycin, normally cannot penetrate the membranes of certain cancer cells.

Similarly, certain diseases could be treated by introducing desired genes into the specific cells of the patient. At present, most gene therapy experiments have utilized retroviruses as the carrier of the gene into the cells. When a retrovirus enters a target cell, it integrates essentially randomly in the genome and thus has the potential for introducing mutational damage by the mere fact of its insertion. If the virus integrates adjacent to an oncogene, malignant transformation of the target cell can result.

It is known that genes and other macromolecules such as pharmacological compounds can be incorporated into live cells through a process known as electroporation. The genes or other macromolecules are mixed with the live cells in a buffer medium and short pulses of high electric fields are applied. The cell membranes are transiently made porous and the genes or macromolecules enter the cells. There they can modify the genome of the cell.

The incorporation of drugs into red blood cells via electroporation as well as the incorporation of genes into white blood cells via electroporation have both been demonstrated. The selective incorporation of genes into white blood cells in whole blood via electroporation has also been demonstrated. The electroporation of cells in a flow-through apparatus has also been demonstrated. Recent methods of gene therapy have used variations of the procedures described above.

One therapeutic application of electroporation consists of the infusion of an anticancer drug and then electroporation of the drug into the tumor by applying voltage pulses between spaced electrodes. The voltage must be adjusted accurately so that the generated electrical field has the desired, optimal amplitude. With external, easily accessible tumors this can be done by applying the electrodes across the tumor, measuring the distance d between the electrodes and selecting the voltage V in the pulse generator so that the electric field $E=V/d$ has the desired amplitude.

It would be desirable to have an automatic control system wherein the distance between electrodes applied to a tumor is automatically fed back to the control system to enable application of the desired voltage pulse.

SUMMARY OF THE INVENTION

Accordingly, it is the primary object of the present invention to provide an improved method of electroporation mediated, in vivo, intra cellular drug and gene delivery for a living patient.

It is another principal object of the present invention to provide an improved apparatus for electroporation mediated, in vivo, intra cellular drug and gene delivery.

My invention provides a useful method and apparatus for introducing macromolecules such as genes and pharmacological compounds into tissue in the body of a patient for therapeutic purposes. A device having spaced electrodes is applied to the body of the patient for generating an electric field at a preselected location within a selected body of tissue. Preselected macromolecules are infused into the selected tissue. Simultaneously an electric signal is applied to the applied device to repeatedly subject a portion of the tissue at the preselected location to electric fields of a predetermined amplitude and duration. The parameters of the electric fields are precisely controlled in order to make the walls of preselected cells in the tissue transiently permeable to permit the macromolecules to enter said preselected cells without killing said cells. The device can include either electrodes inserted into the tissue, or alternatively, electrodes that surround the tissue. The electric signal is supplied by a power pack and the preselected macromolecules are infused with a supply pump.

DESCRIPTION OF THE PREFERRED EMBODIMENTS

Figure 1:
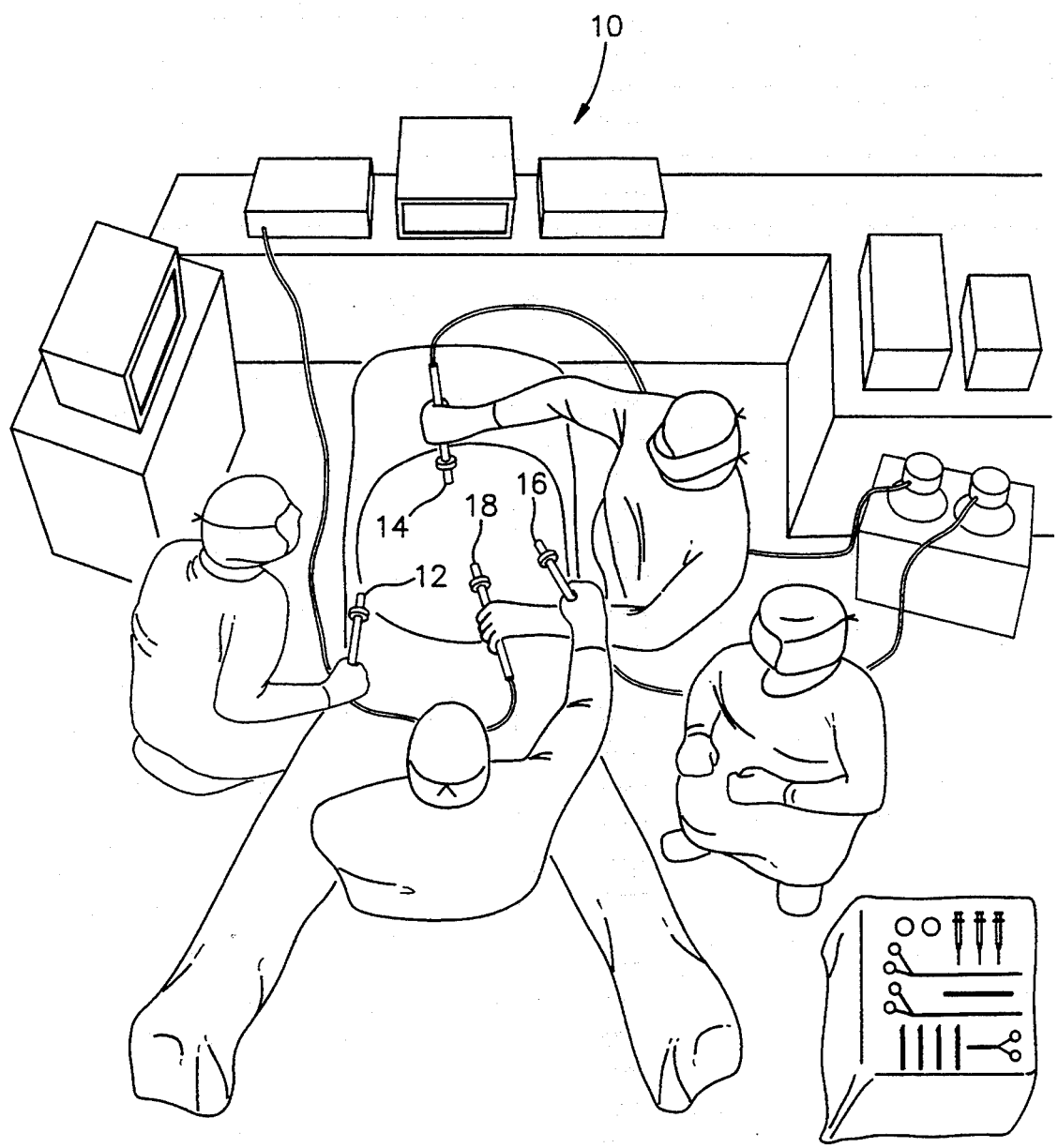
FIG. 1 illustrates an operating room showing a patient undergoing laparoscopic procedures employing the invention.

As used herein the term "macromolecules" includes pharmacological agents, genes, antibodies or other proteins. One human therapeutic application of electroporation consists of infusion of an anticancer drug and electroporation of the drug into the tumor by applying voltage pulses between electrodes (Electrochemotherapy, Mir et al). Referring to FIG. 1, an operating room scene is illustrated wherein a patient is undergoing minimally invasive surgery by laparoscopic techniques. This involves the insertion of small tubes through the abdominal walls through which instruments are inserted to gain access to the abdominal cavity to perform surgery or other procedures therein. In the illustration, laparoscopic instruments 12, 14, 16 and 18 are illustrated in place. The present invention provides instruments and methods to treat such diseases as pancreatic cancer. The invention provides electroporation forceps for use through laparoscopic technique for application to tissue within the abdominal cavity.

Figure 2:
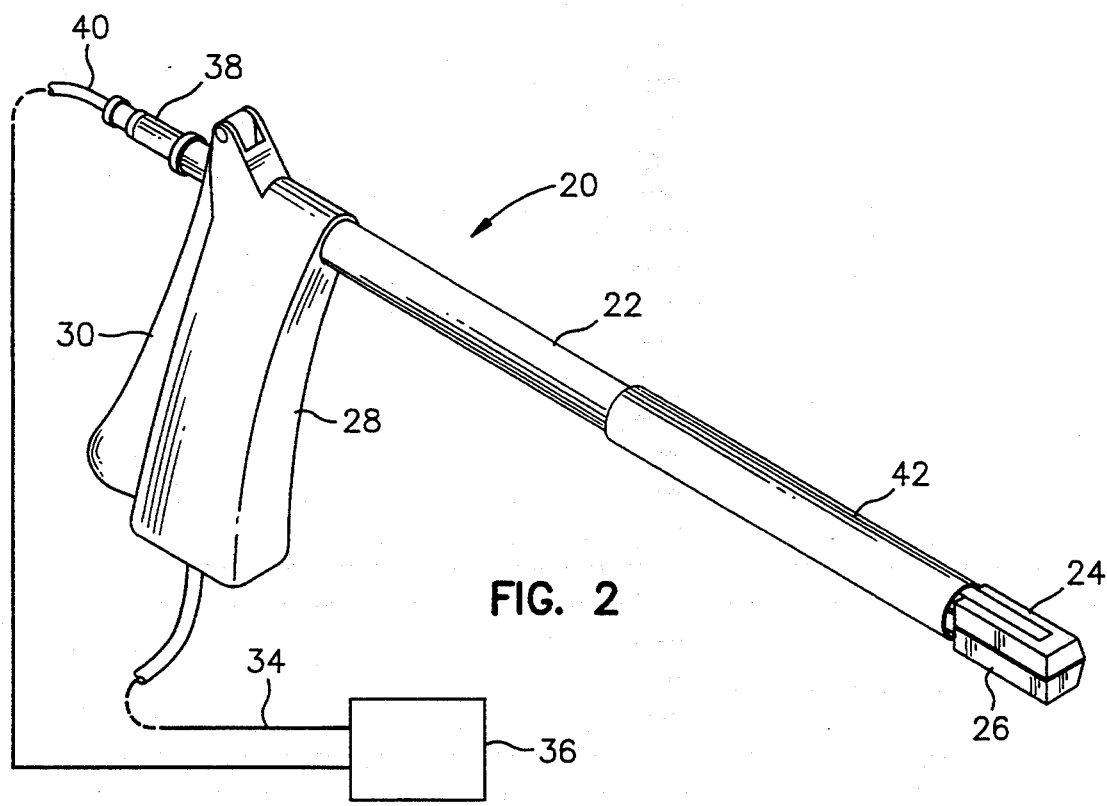
FIG. 2 illustrates a preferred embodiment of the invention for laparoscopic use in the body.
Figure 3:
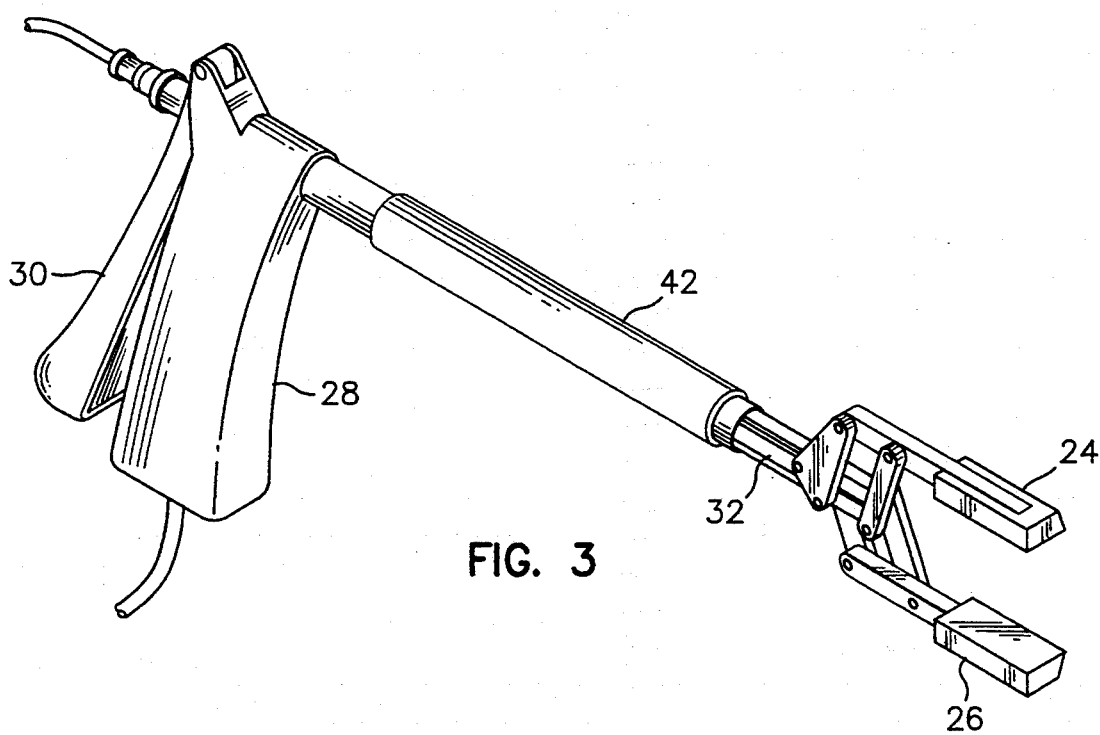
FIG. 3 is a view like FIG. 2 showing the apparatus in a different position of adjustment.

Referring to FIGS. 2 and 3, a preferred embodiment of my apparatus includes a forcep device 20 which comprises a support member 22 having a pair of electrodes 24 and 26 mounted on an insulated linkage of the distal end thereof. A pistol grip handle 28 is mounted on a proximal end of the elongated tubular support member for manipulation of same. The electrodes 24 and 26 are mounted on a moveable linkage so that the electrodes move toward and away from one another like the jaws of a clamp. A movable handle 30 is pivotally mounted at an upper end to grip 28 and connects through a moveable or actuating link 32 to the electrode links controlling the spacing between them. They may be biased by spring means (not shown) acting between grip 28 and handle 30 to the open or outermost position. The electrodes are connected through conductors in a cable 34 to suitable power or pulse generator 36. A suitable sensing unit 38 senses the distance between the electrodes and generates a signal which is transmitted via conductor cable 40 to the pulse generator. A telescopic sleeve or sheath 42 covers the mechanism during insertion.

The distance between the electrodes is one parameter that goes into the adjustment of the voltage to obtain the optimum amplitude of the field. This parameter and its measure and implementation may be sensed and conveyed in many ways. A mechanical indicator coupled to the applicator linkage may provide a readout which the operator enters into the electrical field generating machine. A linear or rotational potentiometer connected to the linkage may provide an electrical signal. The electrode distance may be monitored by a change in capacitance, attenuation of light or other means.

In operation, a unit as above described is inserted into a cavity of a patient via a tube 12 and the electrode jaws are opened and a selected tissue to be treated is placed and gripped between the electrode jaws. The pulse generator connected to the electrodes is then operated by a trigger switch at the unit, a foot switch, or a switch on the instrument panel for repeatedly generating electric fields of a predetermined amplitude and duration in the tissue between the electrodes. The fields are generated by applying a predetermined electric signal to the device. The parameters of the signal are selected so that a the tissue between the electrodes is subjected to short pulses of high intensity electric fields. The voltage is adjusted accurately so that the generated field has the desired, optimal amplitude. These fields make the walls of preselected cells in the tissue transiently permeable to permit the macromolecules to enter said preselected cells without killing said cells. The permeability results from the temporary formation of pores in the cell walls which are large enough to permit migration of the macromolecules through the cell walls.

Figure 4:
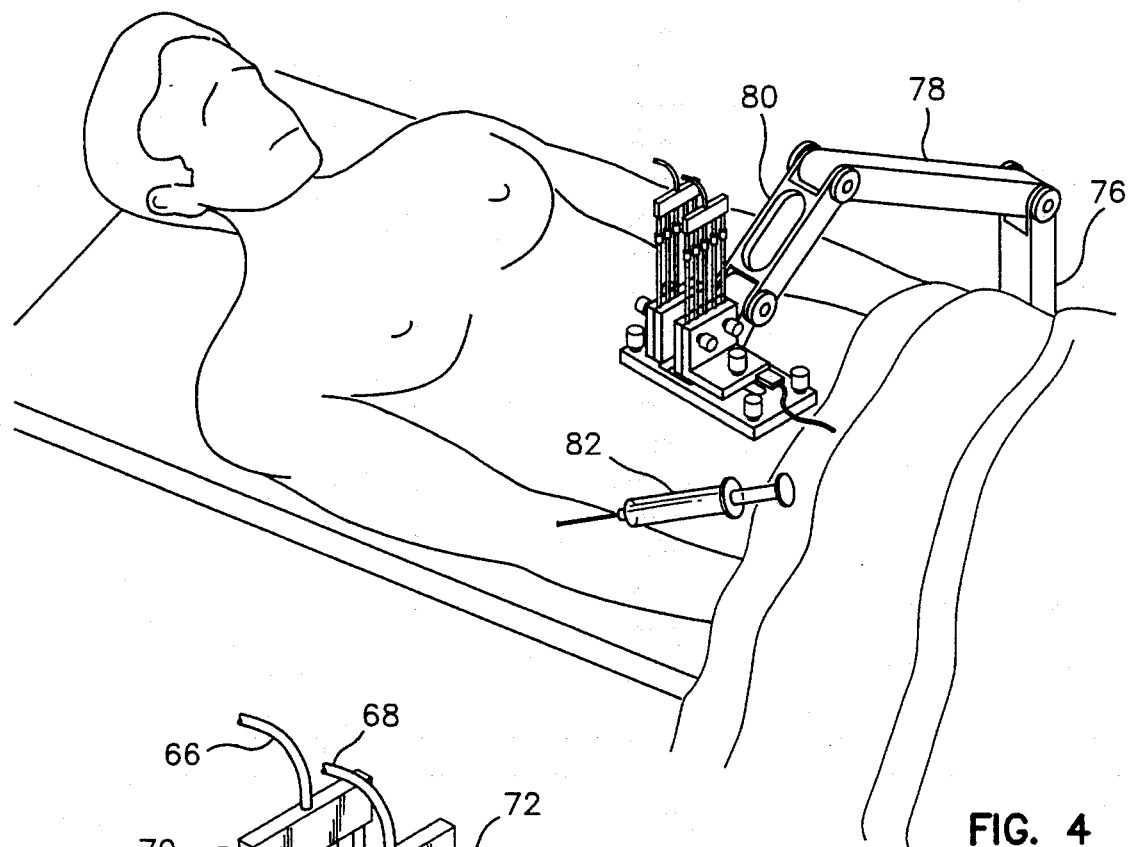
FIG. 4 is a view like FIG. 1 showing an alternate embodiment of electrodes.
Figure 5:
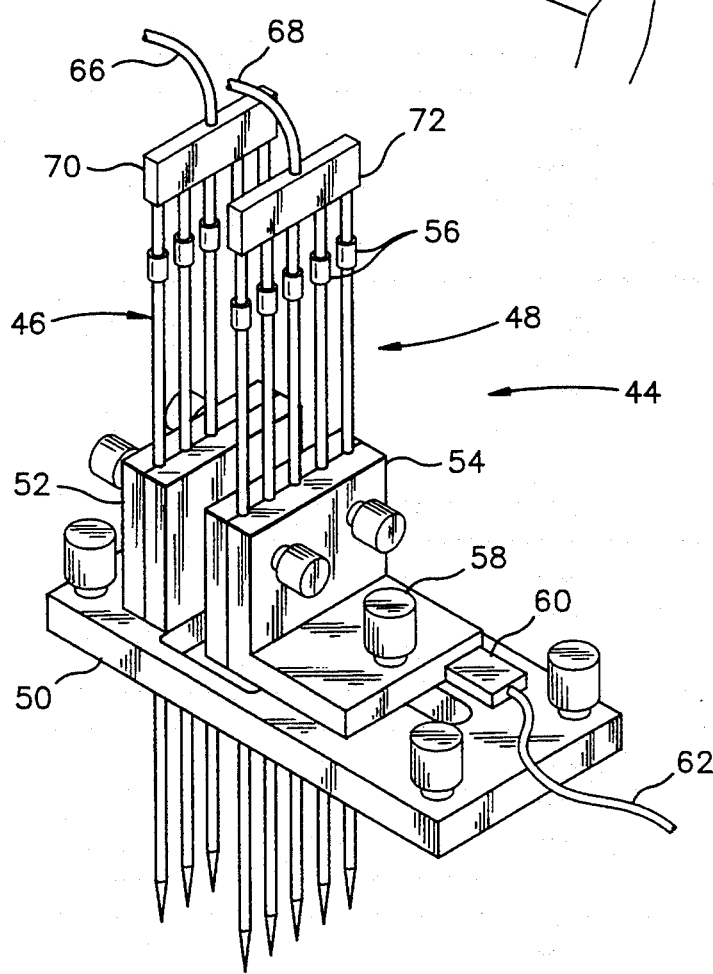
FIG. 5 is a detailed perspective view of the electrodes of FIG. 4.

An alternate embodiment of an electric field generating device is illustrated in FIGS. 4 and 5 and designated generally by the numeral 44. It includes a pair of spaced apart arrays of conductive needle electrodes 46 and 48 mounted on a dielectric carrier or support member 50. The needle array 46 is held in a fixed clamp on the support which allows the needles to be adjusted in depth. The array 48 is held in a moveable clamp which allows the needles to be adjusted in depth and also in distance from the array 46. The needles are each provided with a penetration stop 56. A gap spacing clamp 58 secures the clamp 54 in selected positions on the support 50. A gap spacing sensor 60 senses the distance between the needle arrays and generates a signal that is sent to the pulse generator via conductor cable 62. A pulse generator is connected to the needle electrodes by means of cables 66 and 68 with plugs 70 and 72.

In operation, a unit as above described is selected and mounted on suitable support such as such as a suitable clamp and articulated arm assembly as shown. A post 76 is clamped to the operating table and extends upward with arm 78 hinged to the post and arm 80 hinged on the outer end of arm 78. The support 50 is secured to the outer end of the arm 80. The support 50 is positioned over the patient and the needles of array 46 are inserted into one side of a selected tissue of a patient. The electrodes 48 are positioned at another side of the tissue to be treated and inserted into the tissue. Anticancer drugs are infused into the patient by a syringe 82 or other suitable means.

The pulse generator connected to the electrodes is operated for repeatedly generating electric fields of a predetermined amplitude and duration in the tissue that lies between the electrodes. The fields are generated by applying a predetermined electric signal to the electrodes of the device. The distance between the electrodes is fed into the pulse generator as one paremeter. The distance may be determined any number of ways and fed either manually or automatically into the generator.

Figure 6:
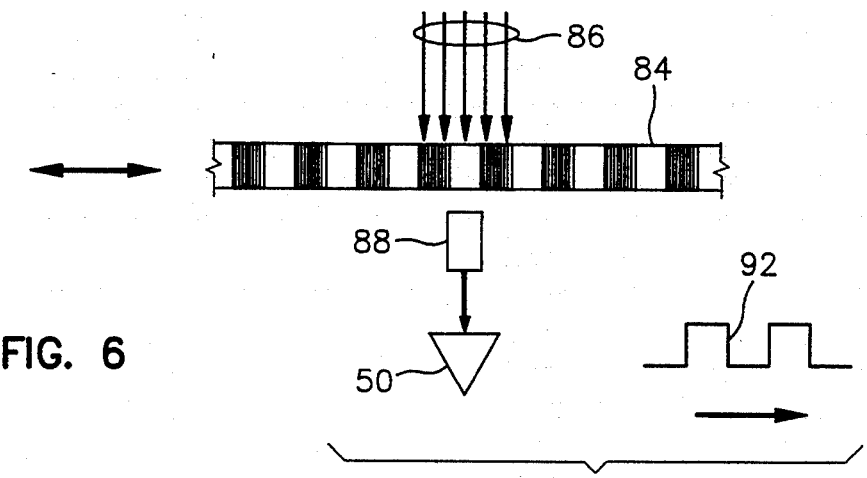
FIG. 6 is a diagrammatic illustration of the electrode position sensor.

Referring to FIG. 6, one example of a digital gap measurement system is illustrated. An optical raster strip 84 is attached to electrode support and moves with the electrode gap. The raster strip is disposed between a light source 86 and a light sensor 88 so that movement of the raster interrupts the light and generates a signal 92 in the sensor 88. The signal is amplified in an amplifier 90 and transmitted to the pulse generator.

The function of the generator in the power pack 36 (FIG. 2) is to generate a predetermined electric signal which, when applied to the electrodes 24 and 26 results in applying electric fields of a predetermined amplitude and duration to the tissue that is clamped between the electrodes. Preferably these fields are applied repeatedly and their amplitude and duration make the walls of preselected cells in the tissue sufficiently permeable to permit the macromolecules to enter the preselected cells. Signal generators capable of generating the required electric fields such as those under the trademark ELECTROCELL MANIPULATOR 600R are available from the assignee BTX, Inc. of San Diego, Calif.

Figure 7:
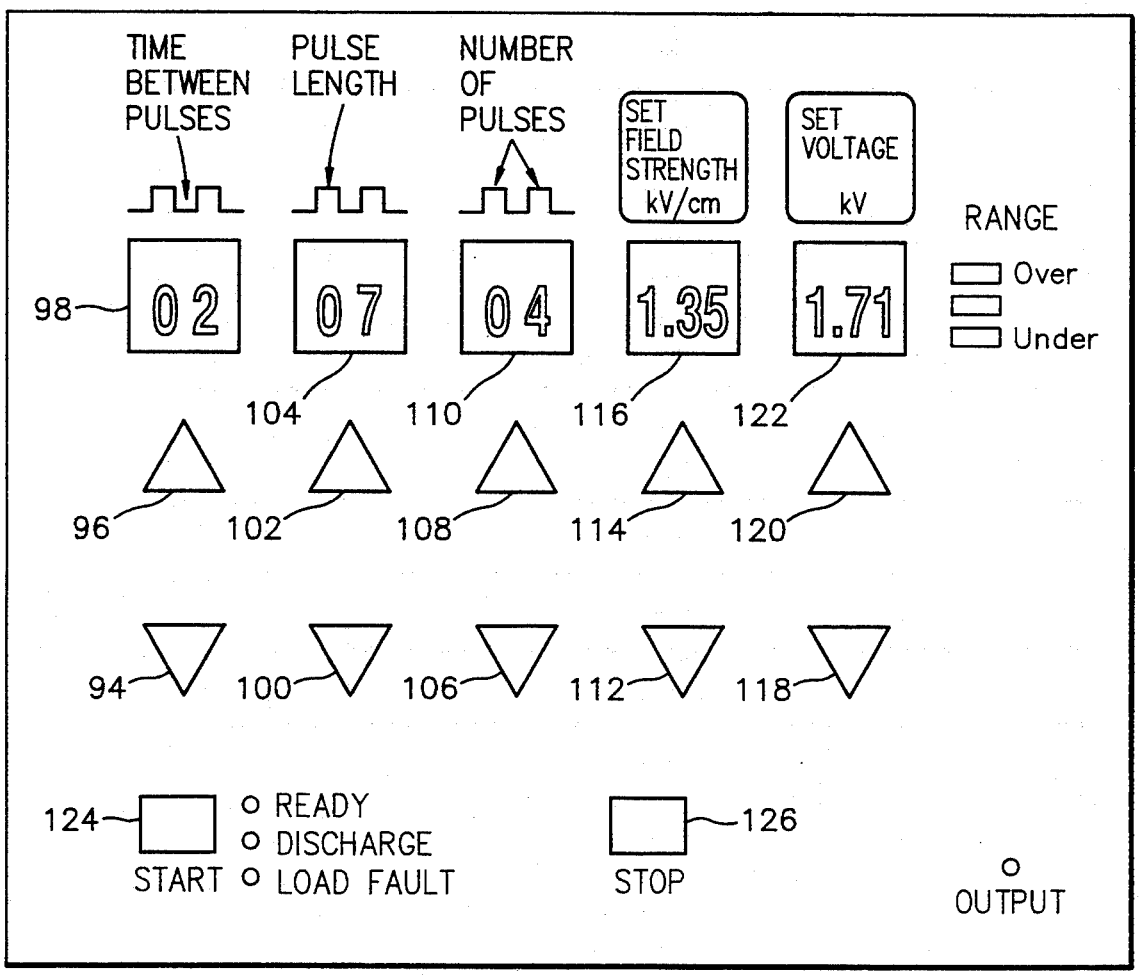
FIG. 7 is an illustration of the control panel for the power supply.

Referring to FIG. 7, one example of a control panel for a pulse power generator is illustrated. In the illustrated panel, the pulse parameters can be selected by switches. The time between pulses can be selected by switches 94 and 96 and read at readout 98. The pulse length can be selected by switches 100 and 102 and read at 104. Switches 106 and 108 selects the number of pulses which is read at 110. The field strength or voltage are selected at switches 112, 114 and 118 and 120 respectively with the values read at 116 and 122 respectively. Start and stop switches 124 and 126 enable starting and stopping the pulse generator.

An electric field across the cell membrane results in the creation of transient pores which are critical to the electroportion process. The pulse power generator provides the voltage (in kV) that travels across the gap (in cm) between the electrodes 24 and 26. This potential difference defines what is called the electric field strength where E equals kV/cm. Each cell species has its own critical field strength for optimum electroporation. This is due to cell size, membrane make-up and individual characteristics of the cell wall itself. For example, some Gram positive bacteria are quite resistant to electroporation and require very high field strengths, i.e., greater than 17 kV/cm, before cell death and/or electroporation occurs. Generally, the required field strength varies inversely to the size of the cell. Mammalian cells require field strengths of typically 200 V/cm to several kV/cm.

The waveforms of the electrical signal provided by the generator in the power pack 36 can be an exponentially decaying pulse, a square pulse, a unipolar oscillating pulse train or a bipolar oscillating pulse train. The electric field strength can be 0.2 kV cm to 20 kV/cm. The pulse length can be ten microseconds to one hundred milliseconds. There can be one to one hundred pulses per per second. Of course the waveform, electric field strength and pulse duration are dependent upon the type of cells and the type of macromolecules that are to enter the cells via electroporation.

While I have described preferred embodiments of my implantable electroporation method and apparatus for drug and gene delivery, it should be understood that modifications and adaptations thereof will occur to persons skilled in the art. Therefore, the protection afforded my invention should only be limited in accordance with the scope of the following claims.

I claim:

1. An apparatus for the therapeutic application of electroporation to a portion of the body of a patient, comprising:
    field generating means including actuating means for adjustably positioning spaced electrodes for generating an electric field at a preselected location within a body of the patient; and
    means for sensing the distance of the space between said electrodes; and
    means for conveying a signal proportionate to the sensed distance to a pulse generator means; and
    pulse generator means responsive to said conveyed signal for applying an electric signal to the electrodes proportionate to the sensed distance between said electrodes for causing the electrodes to repeatedly generate electric fields of a predetermined amplitude and duration forcing the walls of the preselected cells in the body portion to be transiently permeable for enabling molecules to enter said preselected cells.

2. An apparatus according to claim 1 wherein the field generating means comprise forceps having moveable clamping jaws defined by said spaced electrodes.

3. An apparatus according to claim 2 wherein the the forceps include means for insertion through a tube.

4. An apparatus according to claim 3 wherein the forceps comprise a central shaft portion, said clamping jaws positioned on one end of said shaft portion, a handle with actuating means positioned on the other end, and said means for sensing the distance between said electrodes includes means for sensing the relative position of said actuating means.

5. An apparatus according to claim 4 wherein the pulse generator means for applying electric signals to the electrodes includes a pulse power generator for generating an electric field having a strength of between approximately 0.2 kV/cm and 20.0 kV/cm.

6. An apparatus according to claim 5 wherein the pulse power generator generates a electric signal having a wave form selected from the group consisting of an exponentially decaying pulse, a square pulse, a unipolar oscillating pulse train and a bipolar oscillating pulse train.

7. An apparatus according to claim 1 wherein means for sensing the distance and means for conveying a signal proportionate to said sensed distance comprises:
    an optical raster strip attached to move with said actuating means;
    a source of light positioned on one side of said raster; and
    a light sensor positioned on the other side of said raster responsive to sensing light for generating said distance signal.

8. An apparatus according to claim 1 wherein said field generating means comprises an elongated holder;
    at least a pair of conductive electrodes mounted in said holder, at least one of said electrodes moveable relative to the other; and means for sensing the distance between said electrodes and generating a distance signal proportional to said distance.

9. An apparatus according to claim 8 wherein the electrodes are needles.

10. An apparatus according to claim 9 wherein said needles comprise a first plurality of needles mounted in a first clamp fixed on said holder and a second plurality of needles mounted in a second clamp moveably mounted on said holder.

11. An apparatus according to claim 10 wherein the needles include adjustably positionable depth stop means.

12. A method for the therapeutic application of electroporation to a portion of the body of a patient for introducing macromolecules into cells therein, comprising:
    providing field generating means including adjustably spaced electrodes for generating an electric field at a preselected location within the body of a patient;
    sensing the distance between said electrodes and conveying said sensed distance to a pulse generator; and
    applying an electric signal from said pulse generator proportionate to the sensed distance between the electrodes to the electrodes for causing said electrodes to repeatedly generate electric fields of a predetermined amplitude and duration thereby forcing the walls of preselected cells in the body portion to be transiently permeable for permitting the macromolecules to enter said preselected cells.

13. A method according to claim 12 wherein the step of providing field generating means includes providing forceps means having a central shaft portion, moveable electrodes forming clamping jaws on one end of said shaft portion, a handle with actuating means on an other end of said shaft for opening and closing said jaws, and sensing means for sensing the distance between said electrodes including means for sensing the relative position of said actuating means.

14. A method according to claim 13 wherein the electric signal has a wave form selected from the group consisting of an exponentially decaying pulse, a square pulse, a unipolar oscillating pulse train and a bipolar oscillating pulse train.

15. A method according to claim 14 wherein the electric field has a strength of between approximately 0.2 kV/cm and 20.0 kV/cm.

16. A method according to claim 12 wherein the step of providing field generator means includes providing said electrodes in the form of needles comprising a first plurality of needles mounted in a first clamp fixed on a holder and a second plurality of needles mounted in a second clamp moveably mounted on said holder.

* * * * *